(12) United States Patent
Nakao

(10) Patent No.: US 8,480,658 B1
(45) Date of Patent: Jul. 9, 2013

(54) ACTUATION HANDLE FOR A SURGICAL DEVICE WITH MULTIPLE END EFFECTORS

(76) Inventor: Naomi Loew Nakao, New York, NY (US)

(*) Notice: Subject to any disclaimer, the term of this patent is extended or adjusted under 35 U.S.C. 154(b) by 595 days.

(21) Appl. No.: 12/708,122

(22) Filed: Feb. 18, 2010

(51) Int. Cl.
*A61B 17/00* (2006.01)

(52) U.S. Cl.
USPC .............................................. 606/1; 606/113

(58) Field of Classification Search
None
See application file for complete search history.

(56) References Cited

U.S. PATENT DOCUMENTS

| | | | | |
|---|---|---|---|---|
| 5,573,530 | A | * | 11/1996 | Fleury et al. ...................... 606/1 |
| 5,643,248 | A | * | 7/1997 | Yoon ................................. 606/1 |
| 2004/0059345 | A1 | * | 3/2004 | Nakao et al. ................... 606/113 |
| 2004/0267244 | A1 | * | 12/2004 | Erickson et al. ................... 606/1 |
| 2005/0107807 | A1 | * | 5/2005 | Nakao ........................... 606/139 |
| 2011/0306953 | A1 | * | 12/2011 | Pineau et al. ...................... 606/1 |

* cited by examiner

*Primary Examiner* — Bill Thomson
*Assistant Examiner* — Lynsey Crandall
(74) *Attorney, Agent, or Firm* — R. Neil Sudol; Coleman Sudol Sapone, P.C.

(57) ABSTRACT

A handle for a surgical instrument multiple surgical end effectors, the handle being configured to provide a complete and consistent actuation of the different end effectors regardless of whether the instrument is flexible or rigid. The handle is similar in size and configuration to handles of similar single end effector devices.

7 Claims, 14 Drawing Sheets

ACTUATION HANDLE FOR A SURGICAL DEVICE WITH MULTIPLE END EFFECTORS

FIELD OF INVENTION

This invention addresses a novel handle for a surgical instrument having multiple lumens, each lumen designated to house a separate surgical effector. The handle of this invention enables ergonomically favorable, consistently stable deployment of respective surgical effectors, while providing a shape and size akin to that of a single lumen device handle.

BACKGROUND OF THE INVENTION

In a conventional laparoscopic or endoscopic operation, an instrument with a rigid or flexible shaft is inserted into the body through a cannula or working channel of a flexible endoscope. Upon locating a target tissue, a particular surgical effector is deployed through the instrument's lumen, the end effector being visualized by an operator on a video screen. Generally, such instruments are built with a single lumen shaft capable of housing only one such effector. There are, however, several exceptions: certain operations require that several functions are performed in close proximity of time. For such cases, when there is not enough time to allow for the insertion and subsequent withdrawal of multiple instruments, multi-lumen instruments have been devised. In multi-lumen instruments, each lumen houses a different surgical effector, all effectors being part of the same surgical instrument assembly.

U.S. Pat. No. 5,759,187 to Nakao et al, describes such a device for polyp resection and subsequent retrieval. Pursuant to the disclosure of the '187 patent, snare cauterization and retrieval operations are performed with a single surgical instrument assembly comprising a tubular sheath longitudinally divided into two lumens by a septum. One lumen houses a cauterization loop connected to a metal push wire, the wire being slidably disposed in one of the lumens. The second lumen houses an auxiliary loop with flexible web member slidably attached, the web member forming a capture pocket. The loop with capture pocket is operably connected to a second push wire slidably disposed inside the second lumen. A bifurcated handle is operably connected respectively to the cauterization loop and the auxiliary loop with capture pocket. When an arm of the bifurcated handle is actuated, its respective end effector is ejected. The handle of the dual lumen device described in the U.S. Pat. No. 5,759,187 is Y shaped. This Y shaped handle is ubiquitous to other double lumen devices, e.g. devices used for endoscopic retrograde cholangio-pancreatography and devices used for cardiac catheterization and subsequent angioplasty procedures. This handle consists of a lure that extends about the base trunk section, with rigid arms that project from the base of the Y securely linked together.

A similar design is disclosed in U.S. Pat. No. 7,957,417 to Nakao et al, disclosing an instrument solution for removal of common bile duct stones through the Ampulla of Vater. FIG. 37A of the '417 patent demonstrates a triple lumen device with corresponding three pronged handle, each lumen being designated to house an effector with different function.

A cautery retrieval polypectomy snare device with a Y handle described in U.S. Pat. No. 5,759,187 was manufactured and marketed, but had to be withdrawn from use because of several problems that this handle presented. The actuating arm of the snare with retrieval pouch malfunctioned on numerous occasions because the Y configuration of the two actuators: the respective push-rods of the Y handle, as connected to their respective push wires and end effector, were unstable and flimsy due to the angle created by the Y connector. This caused the push rods to buckle or brake off altogether. The problem was exacerbated when the device was used in conjunction with a flexible colonoscope inside a patient's colon. The colonoscope is long and especially tortuous when inserted deeply into the normally convoluted colon. Actuating a bifurcated handle to effect ejection of the retrieval pouch for example, required application of substantial force to that arm of the Y handle, causing buckling of the actuating push rod of the handle. As a result, the retrieval basket could not be consistently ejected from the instrument's double lumen catheter when the colonoscope was deep inside a patient's colon.

Another problem that the Y shaped handles presented was its cumbersome and ergonomically difficult operation for the endoscopist whose hands were occupied wielding the endoscope. Furthermore, such a handle was difficult to package, requiring special packaging designs to support the fragile Y shaped structure. The large size of the package required for the Y shaped handle took up extra shelf space in the operating room, proved costly to sterilize, store, and ship. Furthermore, manufacturing a bifurcated handle increased the price of the instrument, resulting in an ultimate increase in price to the patient.

U.S. application Ser. No. 12/287,717 to Nakao filed Oct. 10, 2008, describes a novel handle for a double-lumen cautery retrieval snare assembly used to cut and retrieve polyps or other lesions in the gastrointestinal tract. This instrument utilizes an electrically conductive cauterization loop end effector, and a flexible auxiliary loop end effector with a flexible web member connected to the loop as described above. The surgical instrument assembly further comprises a tubular sheath or catheter that is longitudinally divided into two lumens. One of the two lumens houses the electrically conductive loop connected to an actuation cable slidably disposed within the lumen. The second contains an auxiliary loop with capture pocket, connected to its own designated cable, slidably disposed inside the second lumen. So far this duplicates the invention taught in U.S. Pat. No. 5,759,187 to Nakao et al. The difference lays in the invention of the handle. The handle disclosed in the patent application Ser. No. 12/287,717 is not bifurcated, but is configured with a single stemmed body, shaped and sized almost identically to handles used in single lumen endoscopic devices. Yet, the handle allows for separate actuations of two different end effectors.

The handle of U.S. application Ser. No. 12/287,717 includes a plurality of actuators disposed in a common plane. The actuators lay adjacent to one another within a single spine handle body. One actuator comprises a thumb ring affixed to a proximal end of the handle body, and a pair of finger rings affixed relative to one another and longitudinally slidable along the handle body. The pair of finger rings is designed to actuate one of the end effectors. A second actuator knob is longitudinally slidable along a handle slot in the handle body, operably connected to the second end effector. The handle assembly contains at least two push rods that lay parallel to one another, one push rod connected to one of the actuators and to a respective push wire slidably disposed within its respective sheath lumen, the cable in turn being connected to a respective end effector. The other push rod is connected to the other actuator and, through its connection to the intervening push wire, is operably connected to a second end effector.

When a prototype of the invention disclosed in U.S. application Ser. No. 12/287,717 was built, this inventor found certain shortcomings in the design. In particular, the actuator knob connection to its respective push rod was too flimsy to function in a consistent manner. The limited real-estate available inside the handle spine precluded a thicker, and thus a more sturdy connection between actuation knob and push wire. Actuation was especially problematic when the instrument assembly was inserted into a biopsy channel of a tortuous flexible colonoscope. Under those conditions, the increased force required to eject the respective end effectors caused the push rods in the handle to buckle under the tension.

OBJECTS OF THE INVENTION

An object of the present invention is to provide an improved, novel design of a handle assembly for a multi-lumen device, this handle having ergonomic advantages over presently existing multi-lumen device handles.

A further object of the present invention is to offer stable, consistent actuation of end effectors in multilumen devices even under the most rigorous conditions of instrument torque.

Another of the present invention is to provide a handle for a multilumen surgical device that would be inexpensive, easily packaged, sterilized, shipped, and stored.

These and other objects will be apparent from the following descriptions.

SUMMARY OF THE INVENTION

The invention disclosed herein constitutes a re-design of the single spine handle of U.S. application Ser. No. 12/287,717. This invention was tested in clinical prototypes, and has proved to work consistently and well. The handle of this invention contains two parallel push rods that lay within the handle spine. These push rods are designed to actuate and eject two respective end effectors. The stability of connection between the actuation members and their respective push rods is achieved by incorporating a toothed design along the entire handle spine, dividing the forces required for actuation. In addition, a specially designed spring member fitted between the actuation knob and the handle spine teeth, along with a two part fitting that holds the spring member stably in line allows for these rather delicate push rods to be actuated under the most severe conditions of instrument torque without buckling or breaking. In addition, this new single spine handle is ergonomically advantageous, and is shaped and sized similarly to a handle used in single lumen instruments.

The handle according with the present invention is utilized as part of a multi-lumen surgical instrument assembly. The instrument may be rigid for use during laparoscopy or flexible for use during an endoscopic procedure. For the purpose of this disclosure, we describe a flexible double lumen cautery retrieval snare used to cut and retrieve polyps or other lesions inside the gastrointestinal tract. This instrument utilizes an electrically conductive cauterization loop attached to a wire, and a flexible auxiliary loop with a flexible web member slidably attached to the loop so as to create an expandable pocket, the auxiliary loop defining the mouth of the pocket. The surgical instrument further comprises a tubular sheath, longitudinally divided into two lumens. One of the two lumens houses the electrically conductive loop attached to a push wire, and the second, an auxiliary loop with capture pocket attached to a respective wire. A handle assembly is operatively coupled to the cauterization snare and auxiliary loop with web member through their respective push wires, so as to enable actuation of these two end effectors independently of one another.

The method of use presented herein below includes the steps of (a) inserting a flexible endoscope into a natural orifice of a patient; (b) using the endoscope to visualize certain hollow internal organs such as intestine; (c) upon detecting an abnormal lesion such as a polyp, moving the double lumen sheath of the instrument assembly through a biopsy channel of the endoscope; (d) actuating a subassembly of the handle to eject the cauterization loop; (e) engulfing the polyp with the cauterization loop, and while activating cautery, severing the polyp from the intestinal wall; (g) actuating a subassembly of the handle to shift the auxiliary retrieval pocket in the distal direction and capturing the transected specimen; (h) withdrawing the endoscope from the patient's body while visualizing the intestinal lumen and retrieved specimen inside the retrieval pocket; and (i) placing the specimen into preservative solution for pathologic examination.

The invention discloses a handle assembly configured for transmitting considerable deployment and retractive forces to two effectors at separate junctures during manipulation of the respective end effectors that are part of this long double lumen instrument. Contrary to the cumbersome Y shaped construction, or other handles with a multiplicity of branched actuators, this handle has the same proportions and size as a handle for a flexible single lumen device. The most significant aspect of the handle assembly of this invention, however, is the even and consistently controlled actuation that each actuation subassembly enables. The novel inventions that bring about the consistently controlled actuation and thereby ejection and retraction of the multiple respective surgical end effectors are described in the two sections directly below. While these descriptions of the handle assembly of this invention refer to a handle used in a double lumen cautery retrieval device used for endoscopic polypectomy, the handle of this invention may be used for other multilumen flexible instruments containing multiple surgical effectors.

For the purpose of this disclosure and as is known in the art, the definition of an "end effector" in rigid and flexible endoscopic devices is an effector that is capable of performing a complete and separate action during a surgical procedure.

DETAILED DESCRIPTION OF THE DRAWINGS

Figure 1:
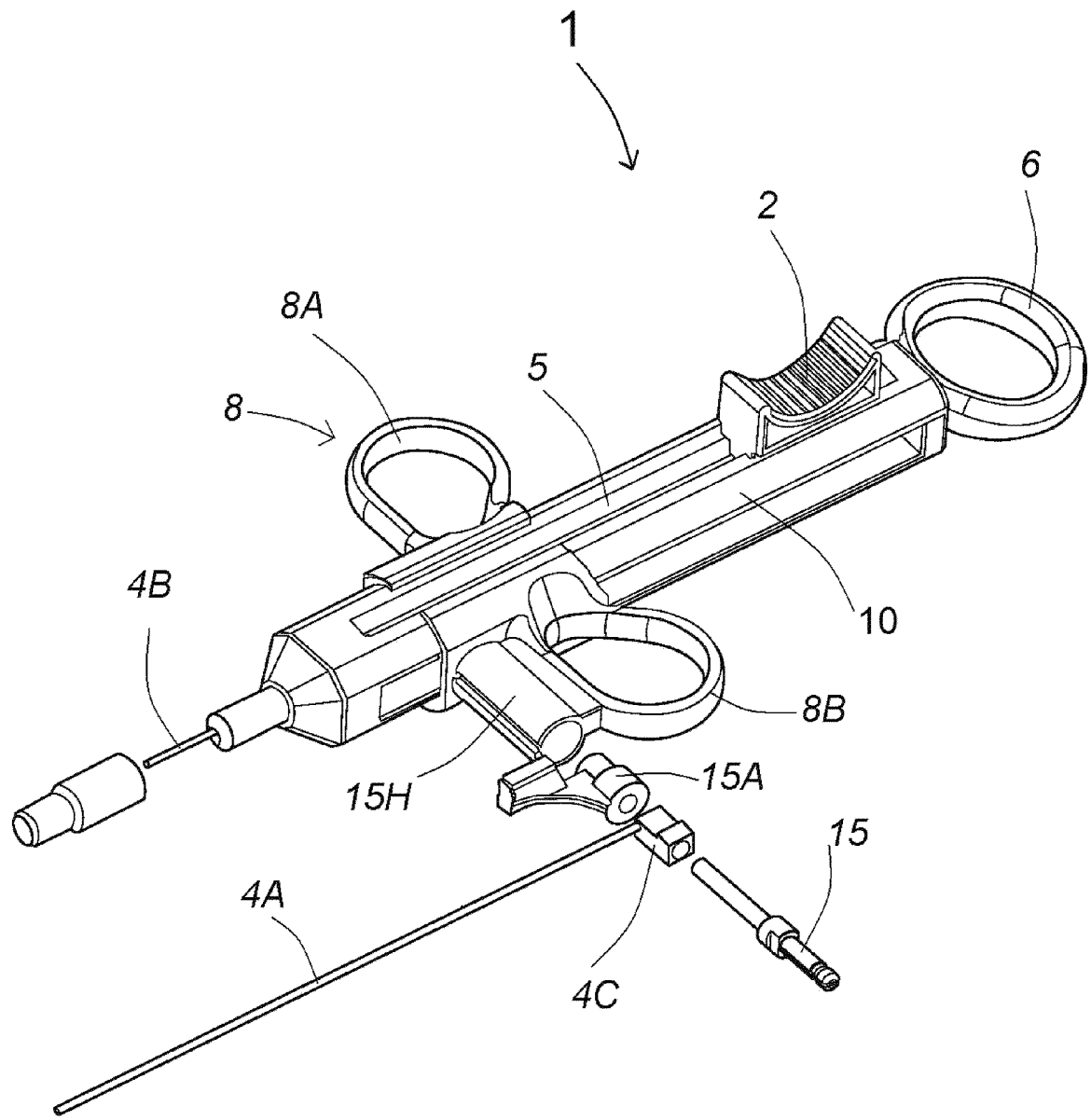
FIG. 1 is a schematic perspective three dimensional view of a partially assembled handle configured for separate actuation of two respective end effectors in a surgical device in accordance with the present invention.
Figure 1A:
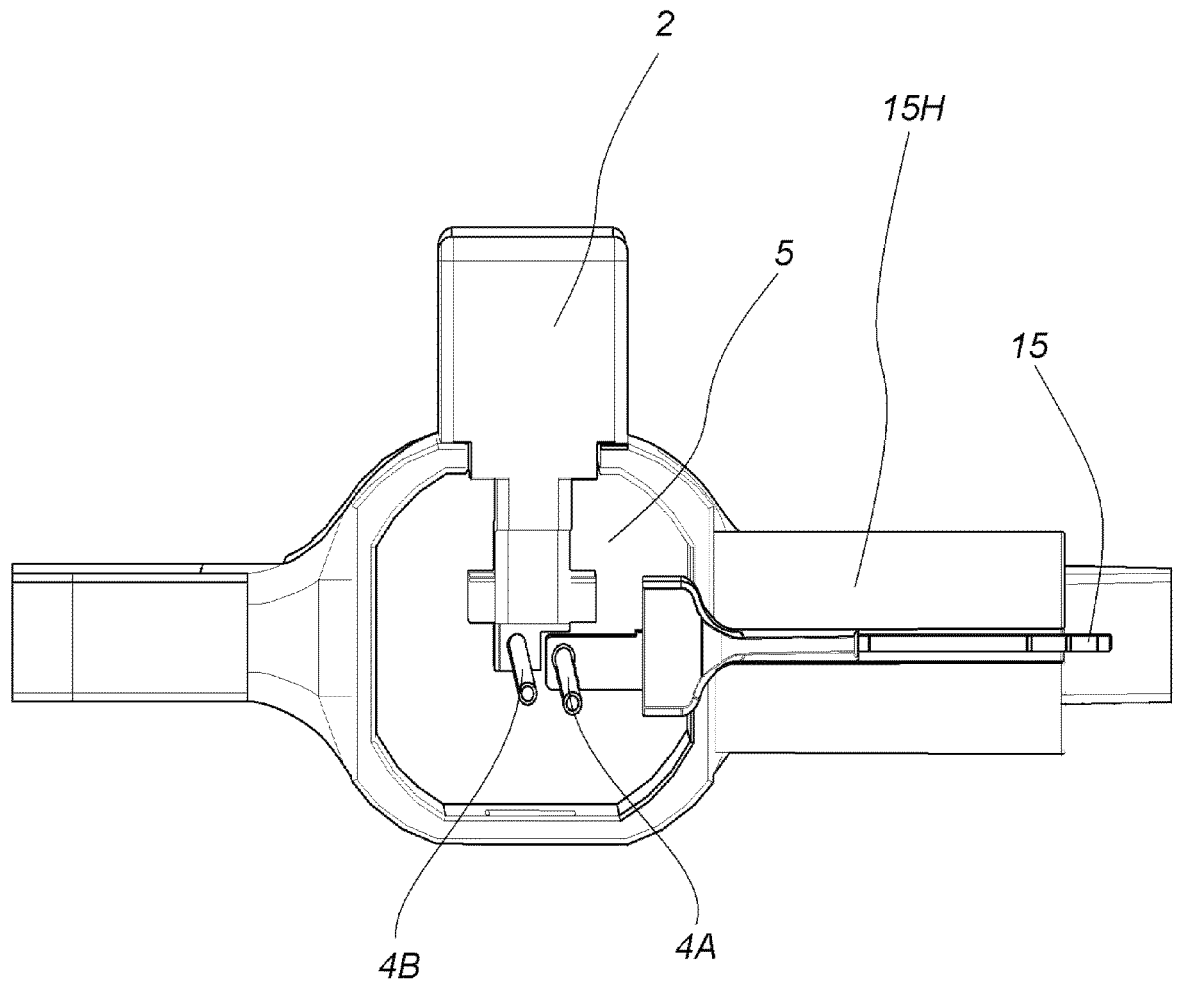
FIG. 1A is a schematic cross sectional view of an assembled surgical instrument handle demonstrating the parallel orientation of two push rods for actuation of two respective end effectors.

As depicted in FIG. 1, handle assembly 1 is configured to control two different end effectors of a surgical instrument. For illustrating the preferred embodiment of the invention, handle assembly 1 is described in a double lumen cautery retrieval polypectomy snare instrument to be used in conjunction with a flexible endoscope. The handle of this invention may be used with other flexible instruments to actuate more than one surgical effector, or as part of a rigid surgical device with more than one end effector. In the case of a cautery retrieval instrument, one handle subassembly controls a cautery snare and the second, a snare with retrieval net. As illustrated in FIG. 1, dual finger ring slide 8 is slidably disposed on handle spine member 10, which comprises longitudinal handle guide or cutout 5, and thumb ring 6, the thumb ring serving as an operator's gripping element. When the handle of the invention is in its assembled configuration, dual finger ring slide 8 is attached to cautery snare hypotube or push rod 4A. A cross sectional view of handle 1 in an assembled state is depicted in FIG. 1A. Hypotube or push rod 4A is connected to a flexible push-wire affixed to an end effector at a distal end thereof, the end effector in this instance being a cautery snare (not shown).

Referring again to FIG. 1, dual finger ring slide 8 is operatively connected to electrode 15, which is connected to electrically conductive cautery snare hypotube or push rod 4A, shown in unassembled state. When assembled, electrode 15 is inserted into electrode molding 15A and attached to cautery snare hypotube 4A either by directly soldering it to hypotube 4A, or by inserting electrode 4A into the opening of cautery snare hypotube adjunct 4C, affixed to cautery snare hypotube 4A.

Figure 3:
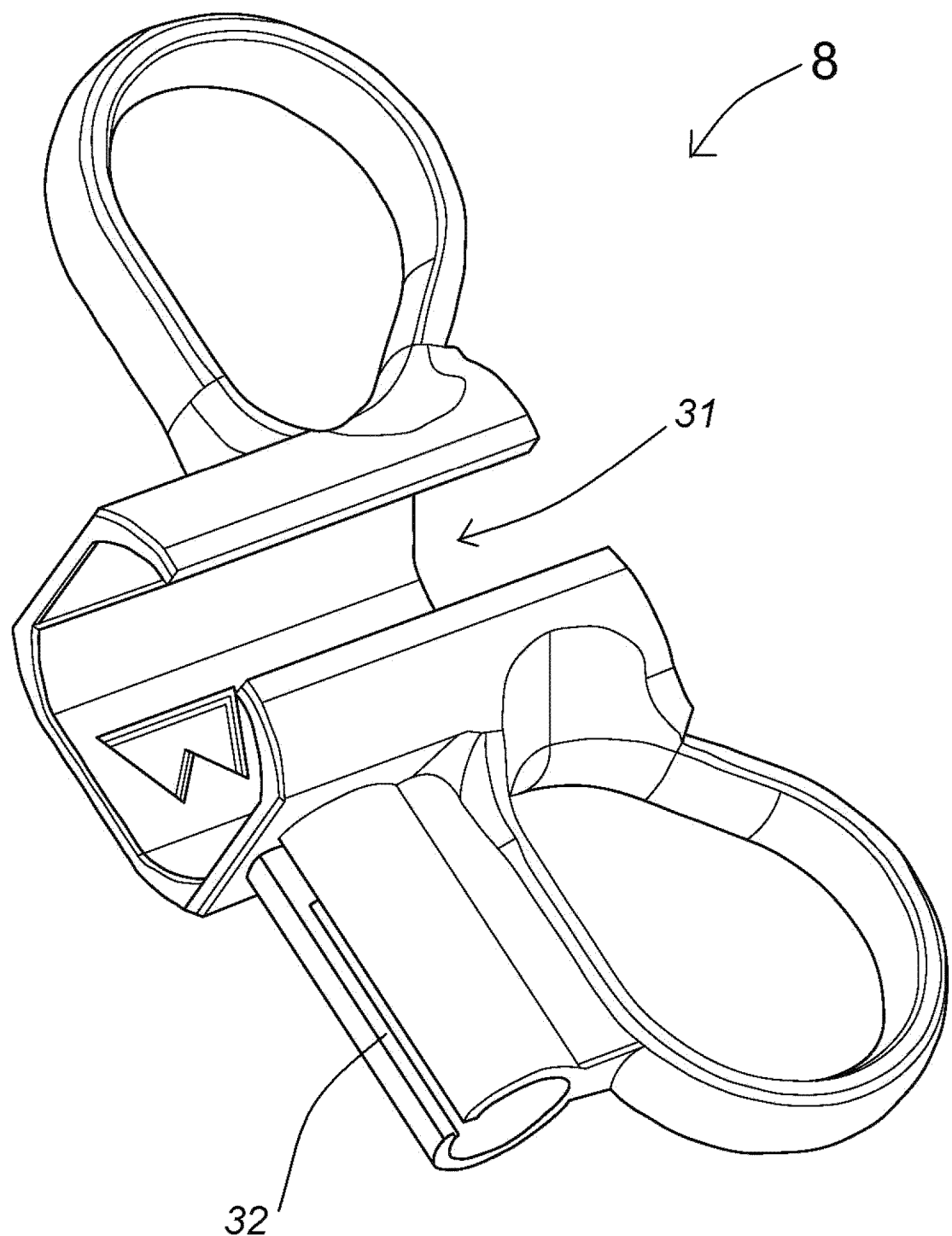
FIG. 3 is a schematic perspective three dimensional view of a dual finger ring slide member of the handle in accordance with the present invention.
Figure 3A:
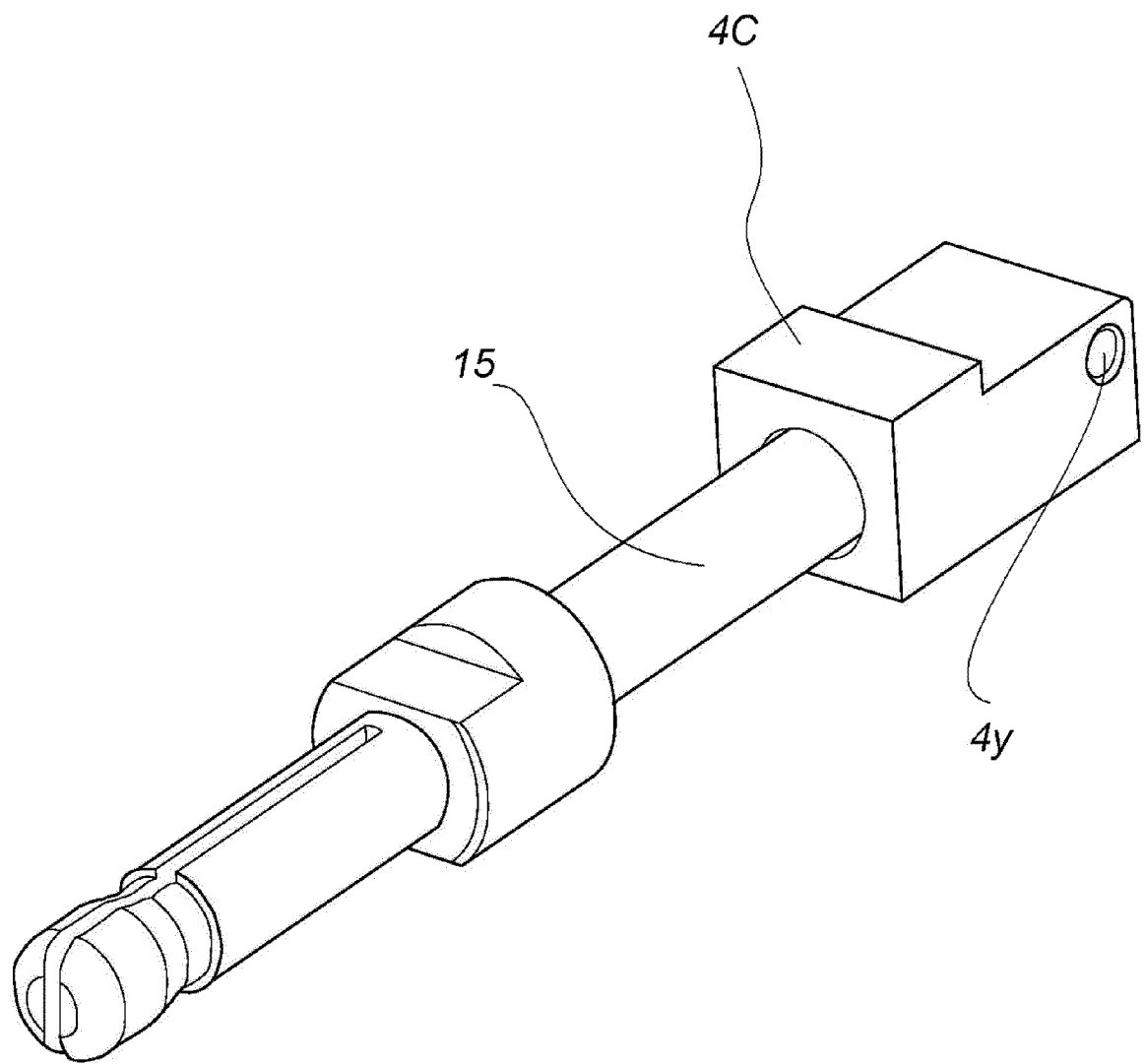
FIG. 3A is a schematic perspective three dimensional view of an electrode and electrode connector of the handle in accordance with the present invention.
Figure 3B:
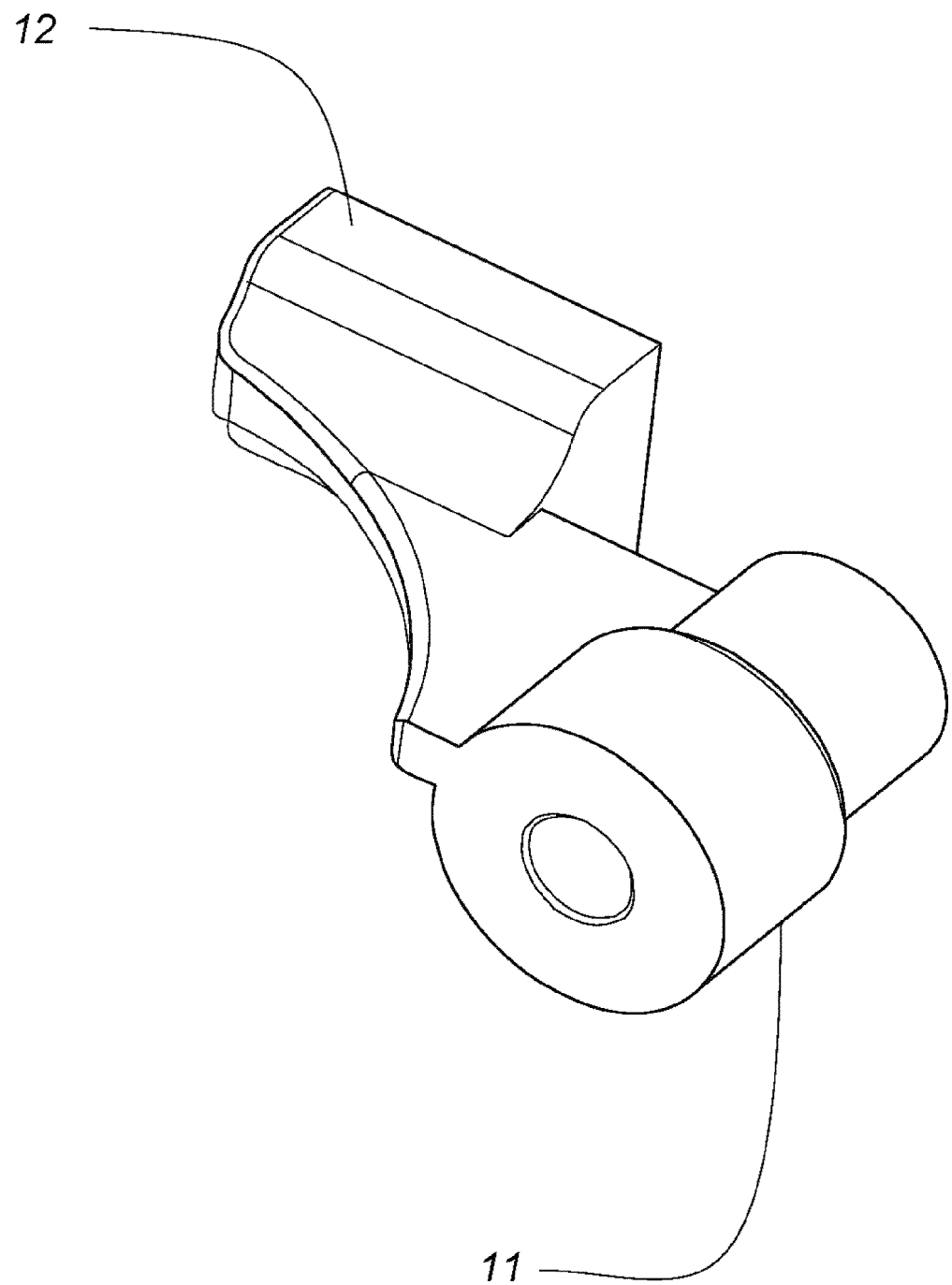
FIG. 3B is a schematic perspective three dimensional view of an electrode molding of the handle in accordance with the present invention.

FIG. 3A is a depiction of electrode 15 coupled with hypotube adjunct 4C. Illustrated here is opening 4y, into which tip 4x of hypotube 4A may be fitted. FIG. 3B is a blown up depiction of electrode molding 15A.

Referring again to FIGS. 1 and 1A, during assembly, hypotube 4A is longitudinally fitted into hollow handle spine member 10. An electrode assembly including electrode molding 15A and electrode 15 is electrically coupled to hypotube 4A is inserted into electrode housing 15H. Conductive cautery snare hypotube 4A is attached to an electrically conductive flexible push-wire coupled at a distal end thereof to a cautery snare end effector (not shown). When dual finger ring slide 8 is actuated from a proximal to a distal direction by an operator engaging thumb ring 6 and finger rings 8A and 8B, cautery snare control hypotube 4A is advanced, thereby advancing attached flexible push-wire and cautery snare end effector. The flexible push-wire and snare end effector are housed in one of two lumens of a flexible double lumen catheter. Upon advancing dual finger ring slide 8 along longitudinal handle cutout 5 of handle spine member 10, an electrically conductive snare end effector is ejected from a distal end of the double lumen catheter (not shown).

Figure 2:
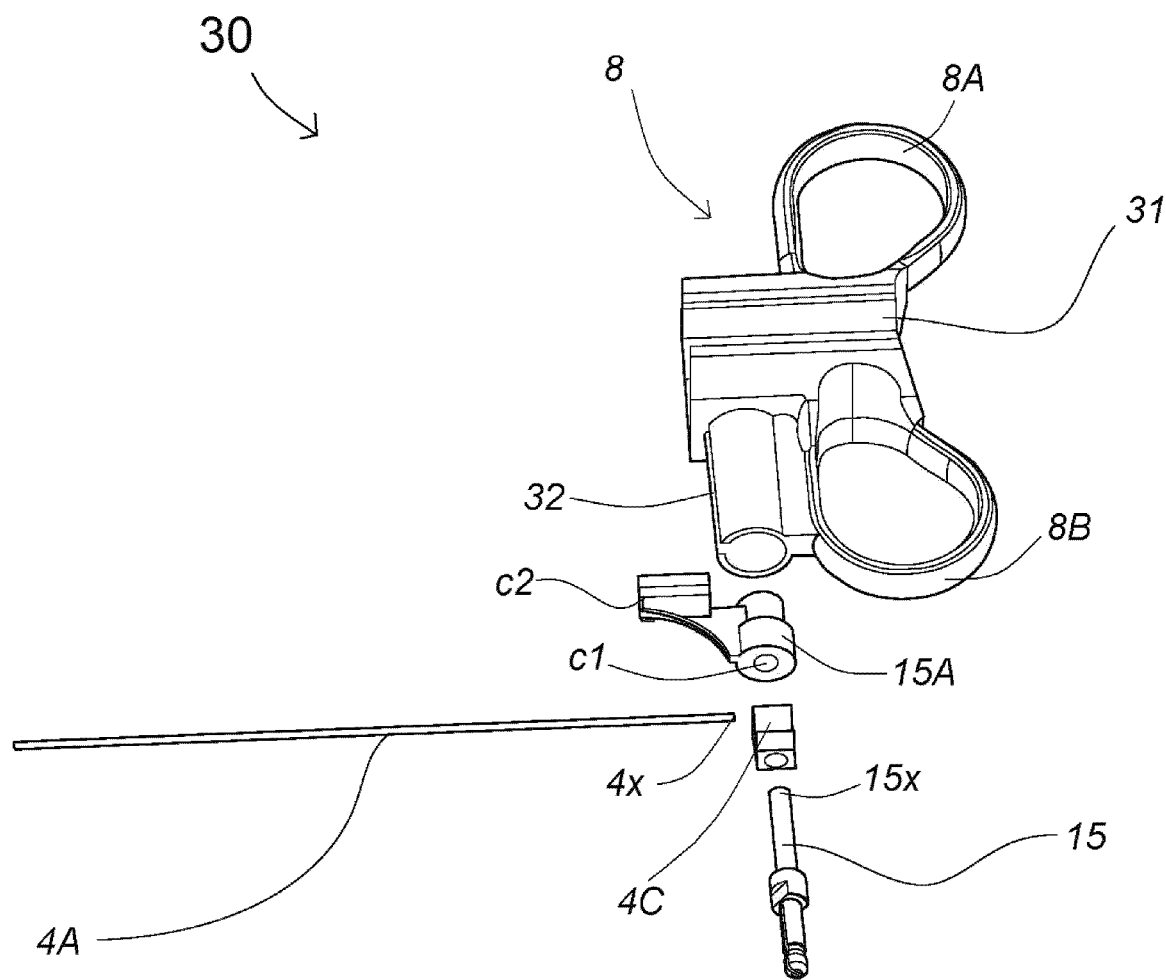
FIG. 2 is a schematic perspective three dimensional view of the parts of a finger ring control subassembly of the handle, in accordance with the present invention.
Figure 2A:
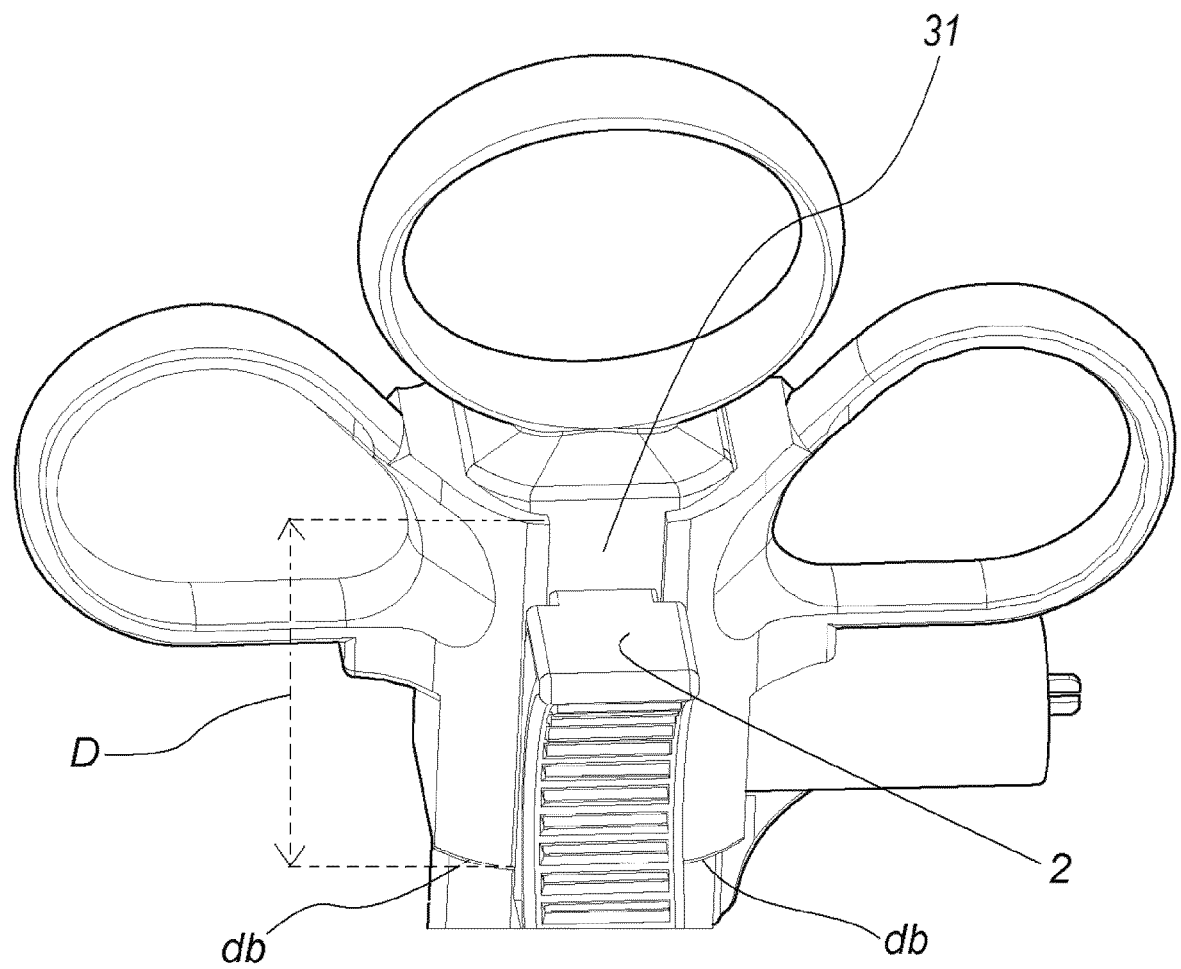
FIG. 2A is a schematic perspective three dimensional view of a thumb knob retracted all the way proximally through a cutout in a dual finger ring slide member of the handle, in accordance with the present invention.

As shown in FIG. 2, finger ring control subassembly 30 is depicted in a pre-assembled state. Dual finger ring slide 8 includes cutout 31. When handle 1 is assembled, cutout 31 is aligned with longitudinal handle cutout 5 as depicted in FIG. 1. Cutout 31 is one of the novel features of this invention. In similar handles used in single end effector instruments, this feature does not exist. The reason for designing finger ring control subassembly 30 to include cutout 31 is illustrated in FIG. 2A. Because of cutout 31, thumb knob 2 designed to actuate the net end effector, may be retracted all the way proximally up longitudinal handle cutout 5 in order to fully retract its respective end effector into the catheter lumen. Without cutout 31, thumb knob 2 would not be retractable beyond, or proximal to the distal boundary (db) of dual finger ring slide 8, reducing the travel distance of thumb knob 2 by distance D, thus preventing complete retraction of the respective end effector. Thus, cutout 31 is provided for a complete actuation of thumb knob actuation subassembly 40 along spine handle 10 cutout 5 without interference by a second actuation subassembly controlled by thumb ring 6 and dual finger ring slide 8, both of these actuation subassemblies being slidable along the same handle spine member cutout 5 without one actuation subassembly interfering with actuation, and bringing about a full through of the other actuation subassembly, and thereby the respective surgical effectors.

As depicted in FIG. 1A, when handle 1 is fully assembled, cautery snare control hypotube 4A is positioned adjacent and parallel to net control hypotube 4B, both hypotubes or push rods being moveably housed at least partially within handle spine member 10. In the case of a cautery retrieval snare or any other instrument provided with electric cautery, this inventor has been mindful of a simple and seamless manufacturing process whereby electrode 15 is fitted into electrode molding 15A. Electrode molding 15A is made of the same or similar hard, nonconductive plastic material that the rest of the handle is made of. As mentioned above, electrode 15 is electrically coupled with electrically conductive cautery snare control hypotube 4A. While the handle of this invention is described for a cautery retrieval snare, it may serve any other end effector requiring electrical conductivity.

Referring to FIG. 2, cutout 32 in dual finger slide 8 was conceived, in accordance with this invention, to enable simpler, less time consuming, and consequently less costly assembly during the manufacturing process. Accordingly, electrode 15 is first coupled with cautery snare hypotube 4A, fitting these electrically conductive parts into specially designed electrode molding 15A. This subassembly is then simply slid through cutout 32 of dual finger ring slide 8 into its designated position inside electrode housing 15H of handle assembly 1.

Similarly to single lumen, single end effector devices, finger rings 8A and 8B are configured for operator's pointer and middle finger to actuate finger ring control subassembly 30 along handle spine member 10. As mentioned above, electrode 15 may be coupled by directly soldering its tip 15x to cautery snare hypotube 4A tip 4x, eliminating the need for cautery snare hypotube adjunct 4C. In that case, electrode 15 would first be inserted into its designated cavity c1 in electrode molding 15A, followed by insertion of tip 4x of cautery snare hypotube 4A into a perpendicular cavity c2 of electrode molding 15A, and then the two conductive members would be soldered together. Alternatively, electrically conductive cautery snare hypotube adjunct 4C could be used as a joint between hypotube 4A and electrode 15, for easier handling of the subassembly process during production.

FIG. 3 depicts dual finger ring slide 8 in a three dimensional perspective view, illustrating more clearly the two novel aspects of the invention, namely cutouts 31 and 32 described herein above.

The second control subassembly depicted in FIG. 1 and in greater detail to be discussed below in FIG. 5, comprises thumb knob 2 affixed to net control hypotube 4B, which in turn is connected to its respective flexible push-wire. The flexible push-wire is connected at a distal end thereof to a second end effector, a snare with retrieval net (not shown). Actuating thumb knob 2 from a proximal to a distal direction advances net control hypotube or push rod 4B causes the flexible push-wire to advance, thereby effecting deployment of snare with retrieval net end effector housed in the other of the two lumens of the flexible double lumen catheter. Upon advancing thumb knob 2 along longitudinal handle guide or cutout 5, the snare-retrieval net is ejected from a distal end of the double lumen catheter.

Figure 4:
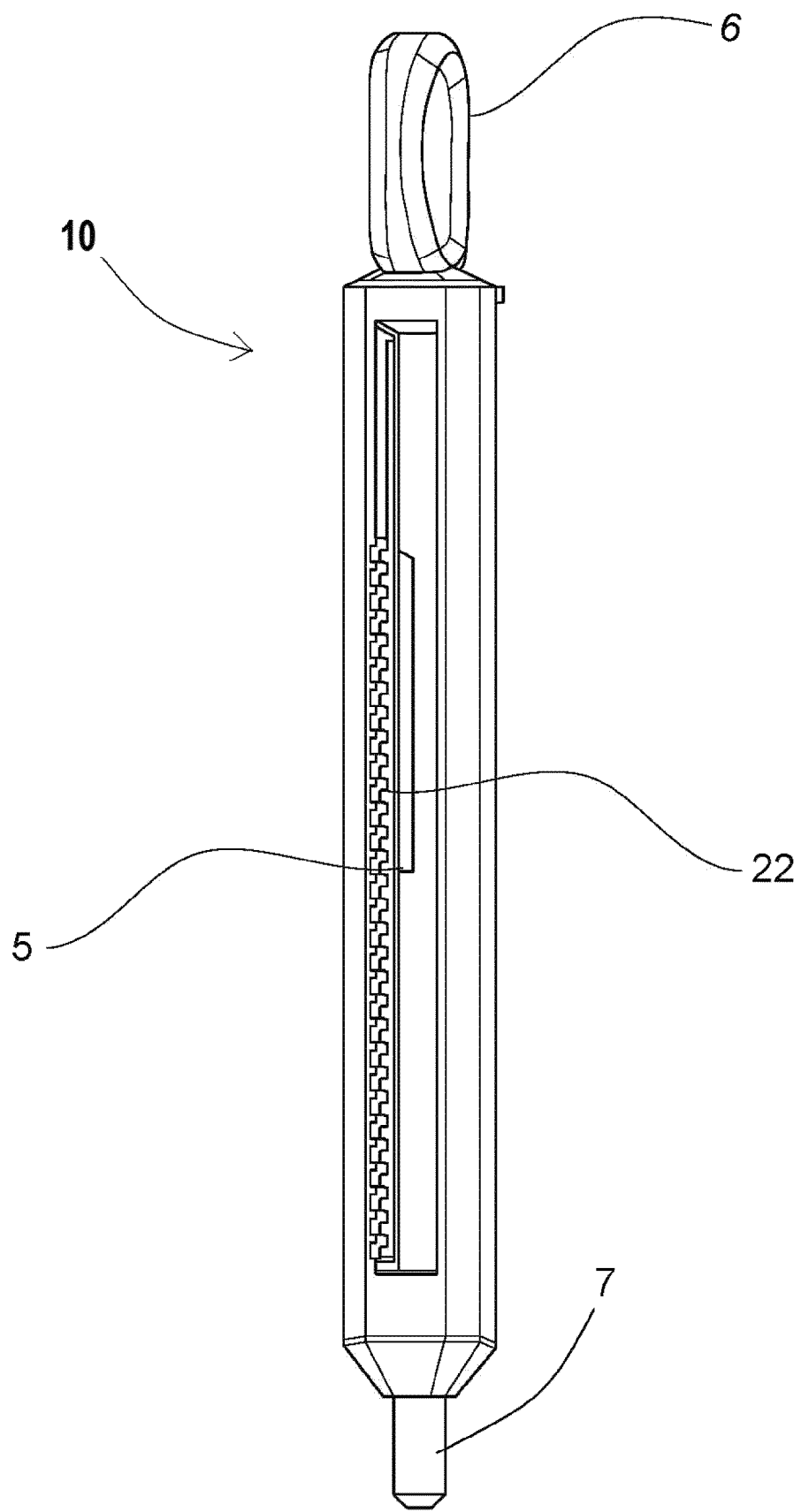
FIG. 4 is a schematic partial perspective three dimensional view of a handle spine subassembly of the handle in accordance with the present invention.
Figure 6:
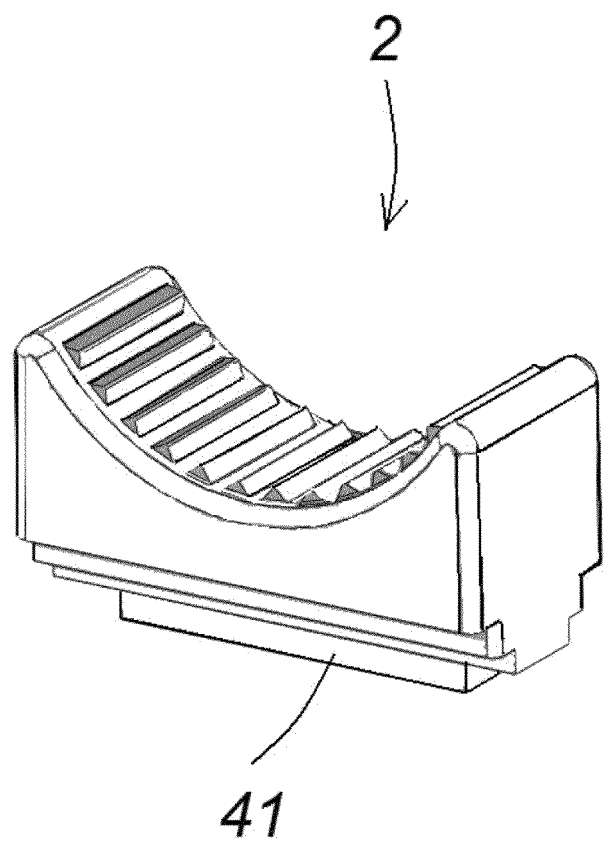
FIG. 6 is a schematic partial perspective three dimensional view of a thumb knob of the handle in accordance with the present invention.
Figure 7:
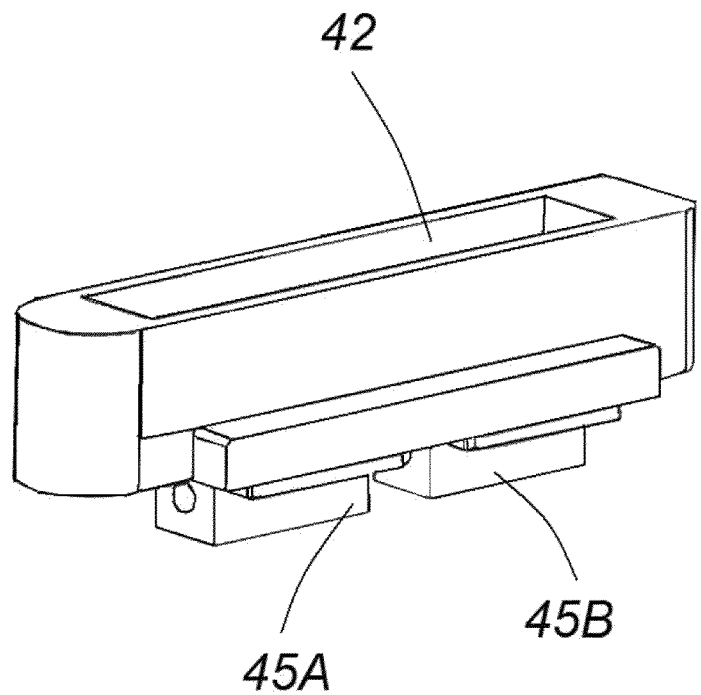
FIG. 7 is a schematic partial perspective three dimensional view of a thumb knob base of the handle in accordance with the present invention
Figure 8:
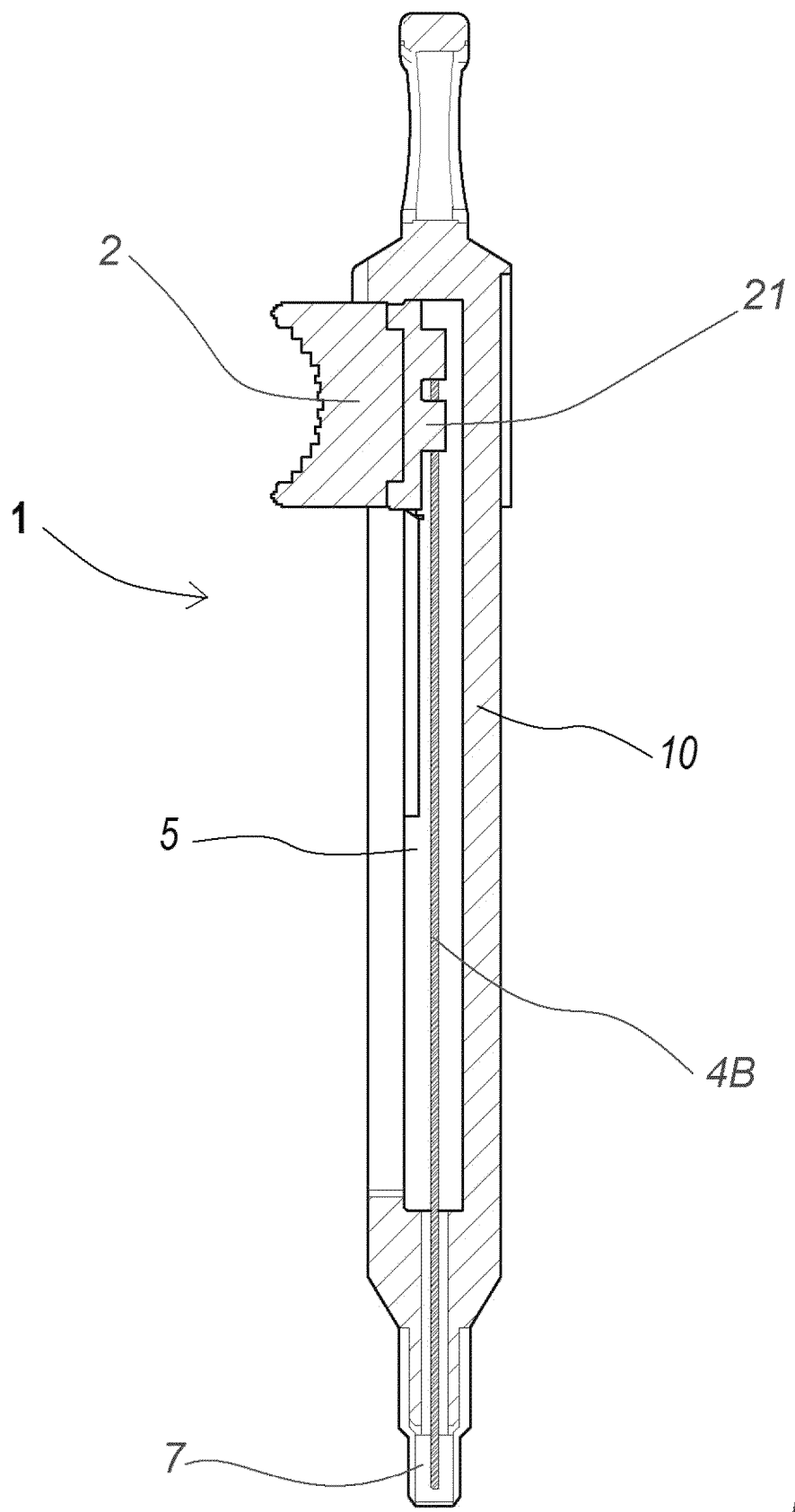
FIG. 8 is a two dimensional rendering of a handle assembly including a thumb control subassembly in accordance with the present invention.

FIG. 4 illustrates handle spine 10, comprising thumb ring 6, nose tube 7, ratchet teeth 22, and longitudinal handle cutout 5. Another important novelty of this invention is the mechanical interaction between teeth 22 of handle spine 10 and sliding thumb control subassembly 40 shown in FIGS. 5 and 5A. Now referring to FIGS. 5 and 5A, thumb knob 2, also shown separately in FIG. 6 fits into thumb knob base 21 shown separately in FIG. 7. As illustrated in FIG. 6, stepped projection 41 of thumb knob 2 fits into recess 42 in thumb knob base 21 shown in FIG. 7. Even more specifically, thumb knob 2 and thumb base 21 are designed to fit together on either side of handle spine member cutout or guide 5 as depicted in a two dimensional drawing of handle 1 shown in FIG. 8.

Referring again to FIGS. 5 and 5A, net control hypotube 4B is insertable into thumb base hypotube housings 45A and 45B, and may be fastened in place by crimping hypotube 4B between hypotube housings 45A and 45B, and at a point proximal to housing 45B. This is one important feature of this invention overcoming the problem of instability. The second feature conceived to stabilize ejection and retraction of the respective end effectors is described below.

Figure 9:
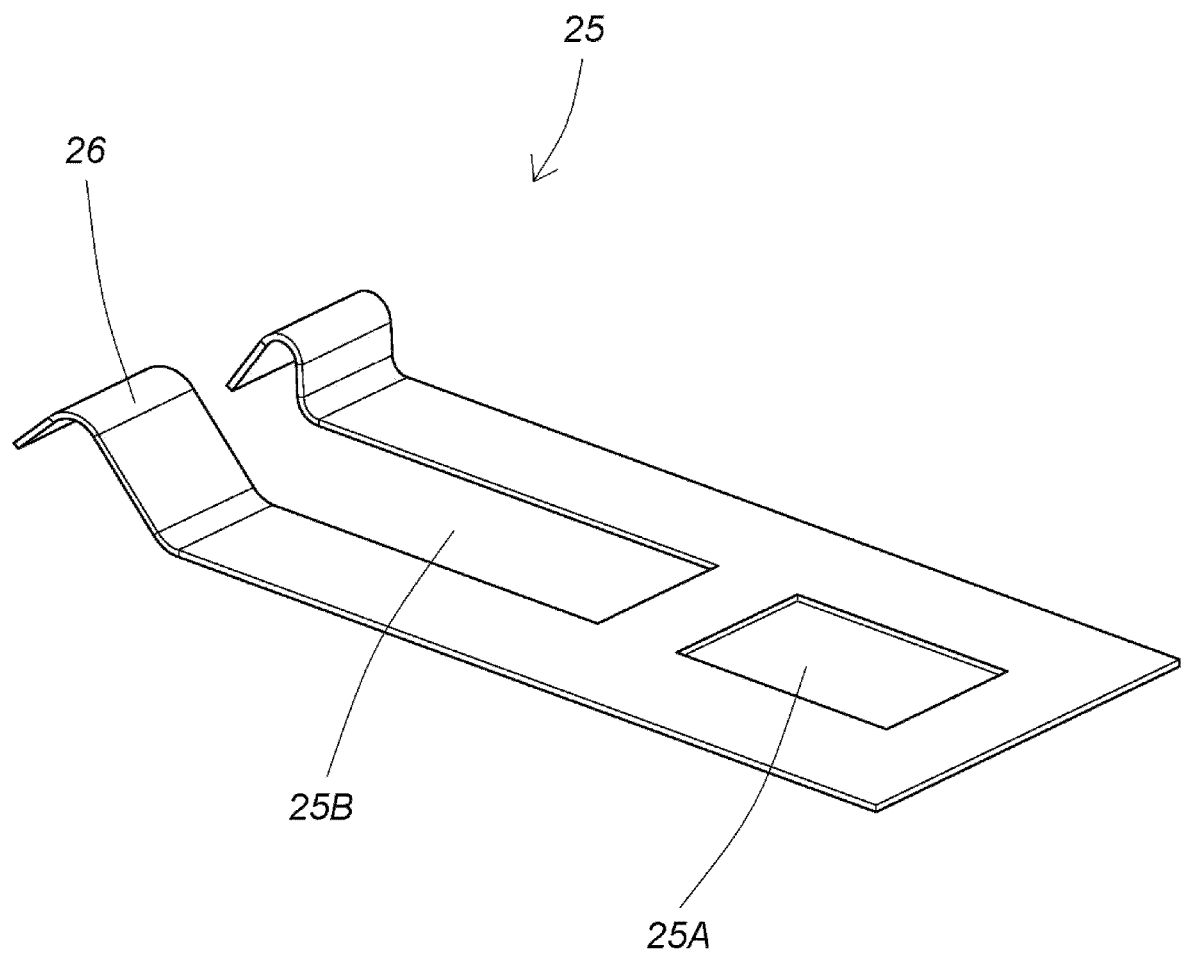
FIG. 9 is a schematic partial perspective three dimensional view of a spring of the thumb control subassembly in accordance with the present invention.

FIG. 9 is a depiction of spring 25, which, along with teeth 22 of handle spine member 10 constitutes the second feature invented to stabilize and create a uniformly consistent sliding mechanism of thumb control subassembly 40 along longitudinal handle cutout 5 of handle spine member 10, thereby bringing about distribution of forces along the greater part of handle spine member 10, and thus a consistently flawless ejection and retraction of the respective end effector even under the most extreme conditions of instrument torque.

Figure 5:
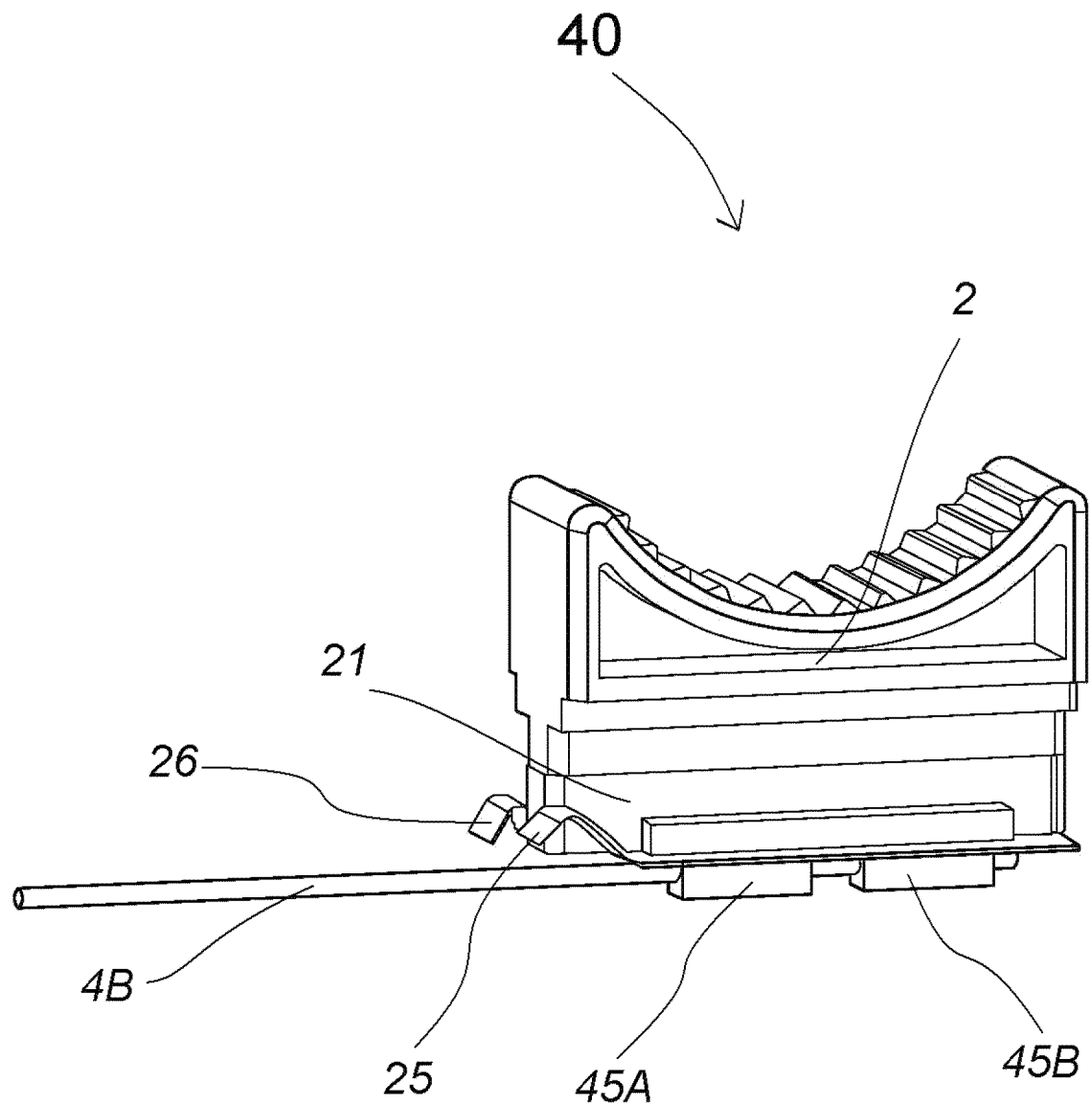
FIG. 5 is a schematic partial perspective three dimensional view of a thumb control subassembly of the handle in accordance with the present invention.
Figure 5A:
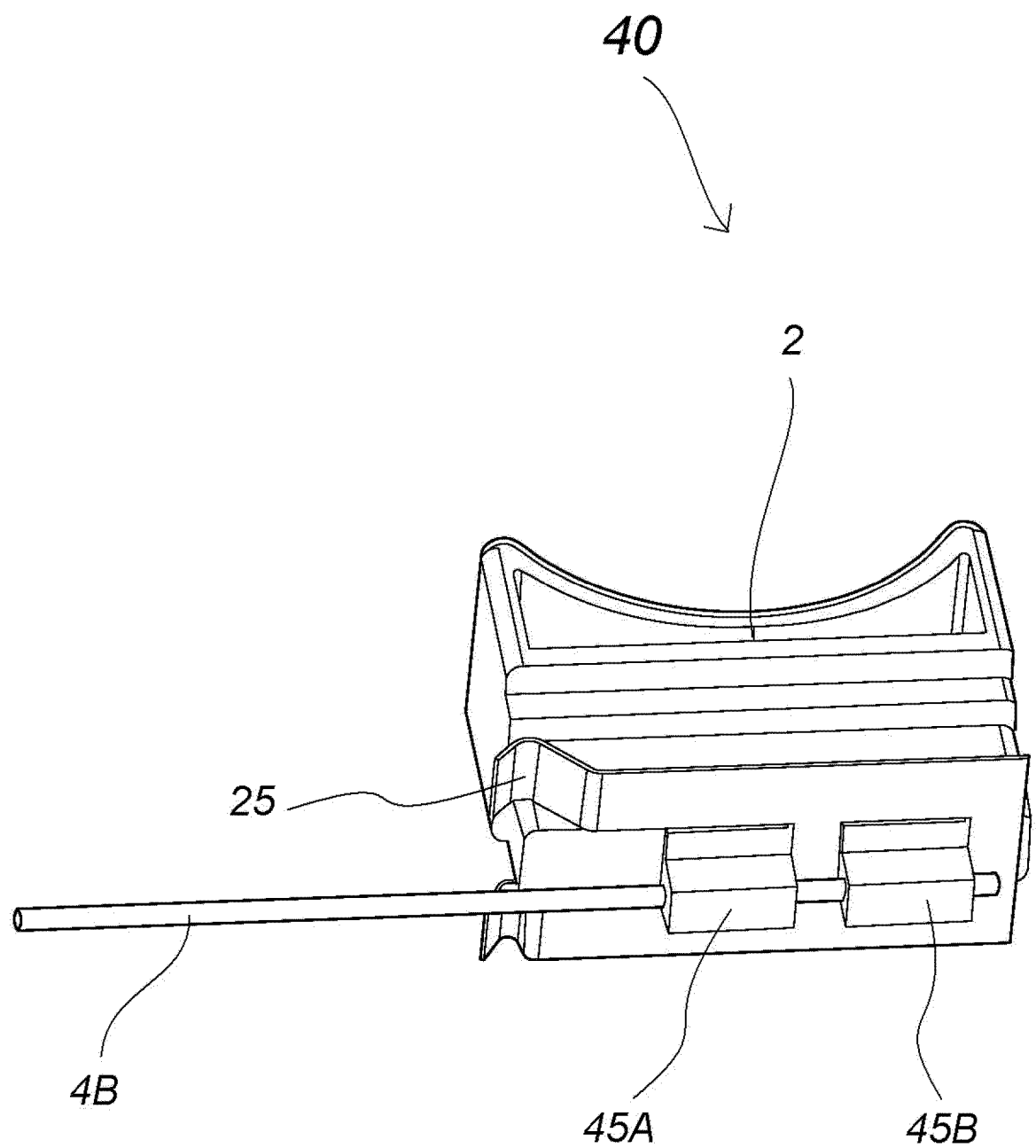
FIG. 5A schematic partial perspective partially rotated three dimensional view of a thumb control subassembly of the handle in accordance with the present invention.

As shown in FIGS. 5 and 5A, slide-action-stabilizing spring 25 is fitted to and positioned beneath thumb knob base 21 with stepped hypotube housing 45A and 45B protruding through spring cutouts 25A and 25B shown in FIG. 9. When sliding thumb control subassembly 40 is in its assembled state in handle assembly 1, spring shoulder 25 abuts the crevices between teeth 22. As a result, when sliding thumb control subassembly 40 is moved along handle spine subassembly 10, an operator perceives a uniformly consistent sensation of this slide-action-stabilizing mechanism accompanied by a controlled actuation along the length of designated cutout 5 of handle spine member 10. In addition to being ergonomically beneficial, this system distributes the actuating force applied by the operator along a substantial length of the handle spine, preventing buckling of end effector control hypotube 4B. This mechanism ensures consistent actuation in a multi-lumen flexible instrument used inside a biopsy channel of a tortuously positioned flexible endoscope placed within a patient's tortuous internal organ.

What is claimed is:

1. A handle assembly for a surgical device with multiple independently operable end effectors for performing respective different operations on tissue, said handle assembly comprising:
   a handle spine configured with a longitudinal cutout or guide; and
   at least two actuation control subassemblies, each one of said actuation control subassemblies being operably connected to a respective one of said end effectors, each one of said actuation control subassemblies being slidably disposed at least partially within said cutout or guide of said handle spine; whereby
   each one of said actuation subassemblies contains a push rod member coupled at a proximal end thereof with at least one corresponding gripping element, and at a distal end thereof, operably connected to a respective one of said end effectors; whereby
   said push rod members are positioned along said cutout or guide in a substantially parallel relationship to one another; and whereby
   the actuation of each one of said push rod members caused by an actuation of said corresponding gripping elements effects an actuation of the respective one of said end effectors.

2. The handle assembly of claim 1, wherein one of said actuation control subassemblies comprises a subassembly including a thumb knob and a thumb base, wherein said thumb knob is slidably disposed upon one side of said cutout or guide; and
   said thumb knob base being slidably disposed on another side of said cutout or guide; wherein
   said thumb knob and said thumb knob base being configured with respective projections and recesses with said thumb knob projections fitting into respective recesses of said thumb knob base, said thumb knob being supported by said thumb knob base; and wherein
   said thumb knob base is fixedly attached to a corresponding one of said push rod members.

3. The handle assembly of claim 2, wherein said thumb knob base is provided with hypotube housings and wherein a control hypotube is insertable into said hypotube housings of said thumb base.

4. The handle assembly of claim 1, further comprising a stabilizing spring subassembly including a stabilizing spring; whereby
   said stabilizing spring is provided with one or more cutouts, and one or more shoulders.

5. The handle assembly of claim 1, wherein said handle spine has a long axis whereby said actuation subassemblies are slidably disposed in juxtaposition with said handle spine such that actuation of each one of said actuation subassemblies occurs in a substantially parallel path to said long axis of said handle spine; and whereby
   said handle spine is provided at said longitudinal cutout or guide with ratcheting teeth with crevices configured therebetween.

6. The handle assembly of claim 4 wherein said stabilizing spring subassembly is provided with ratcheting teeth with crevices there between, wherein at least one of said shoulders of said stabilizing spring abut the crevices between said ratcheting teeth.

7. A handle assembly for a surgical device with multiple end effectors, said handle assembly comprising:
- at least two actuation control subassemblies, each one of said actuation control subassemblies being operably connected to a respective one of said end effectors, each one of said actuation control subassemblies being slidably disposed at least partially within a handle spine cutout or guide;
- at least two push rod members each actuatable by a corresponding one of said actuation subassemblies to effect an actuation of a respective one of said end effectors; and wherein
- one of said actuation subassemblies comprises a thumb knob and a thumb knob base subassembly including a thumb knob and a thumb knob base wherein said thumb knob and thumb knob base are configured with respective projections and recesses with said thumb knob projections fitting into respective ones of said recesses, said thumb knob being supported by said thumb knob base and fixedly attached to a corresponding one of said push rod members; and wherein
- said thumb knob and thumb base subassembly is provided with hypotube housings wherein a control hypotube is insertable into said hypotube housings,
- said handle further comprising a handle spine having a long axis whereby said actuation subassemblies are slidably disposed in juxtaposition with said handle spine such that actuation of each one of said actuation subassemblies occurs in a substantially parallel path to said long axis of said handle spine; and whereby
- said handle spine is provided at said longitudinal cutout or guide with ratcheting teeth with crevices configured therebetween;
- said handle also being provided with a slide stabilizing spring subassembly comprising a slide stabilizing spring configured with one or more cutouts and one or more shoulders, wherein at least one of said shoulders abuts the crevices between said ratcheting teeth, and whereby said spring is configured to fit into said thumb knob and thumb base subassembly.

\* \* \* \* \*